United States Patent [19]

Yamada et al.

[11] Patent Number: 5,092,885

[45] Date of Patent: Mar. 3, 1992

[54] PEPTIDES WITH LAMININ ACTIVITY

[75] Inventors: Yoshihiko Yamada, Silver Spring, Md.; Jeannette O. Graf, Glen Oaks, N.Y.; Yukihide Iwamoto, Higashi, Japan; Frank Robey; Hynda K. Kleinman, both of Bethesda, Md.; Makoto Sasaki, Wheaton, Md.; George R. Martin, Bethesda, Md.

[73] Assignee: The Government of the United States of America as Represented by the Secretary of the Department of Health and Human Services, Washington, Del.

[21] Appl. No.: 272,165

[22] Filed: Nov. 16, 1988

Related U.S. Application Data

[63] Continuation-in-part of Ser. No. 102,991, Oct. 1, 1987, abandoned, which is a continuation-in-part of Ser. No. 13,919, Feb. 12, 1987, abandoned.

[51] Int. Cl.$^5$ .............................................. A61F 00/00
[52] U.S. Cl. ........................................ 623/11; 623/66; 623/1
[58] Field of Search .................. 623/1, 66, 11; 514/8, 514/9; 530/300, 317

[56] References Cited

U.S. PATENT DOCUMENTS

| | | | |
|---|---|---|---|
| 4,497,799 | 2/1985 | Yoshizumi et al. | 514/9 |
| 4,614,517 | 9/1986 | Ruoslahti et al. | 623/66 X |
| 4,714,683 | 12/1987 | Shoyab et al. | 530/300 X |

FOREIGN PATENT DOCUMENTS

WO84/00540 2/1984 World Int. Prop. O. .

OTHER PUBLICATIONS

Barsky et-al., "Laminin Molecular Domains which alter Metastasis in a Murine Model", J. Clin. Invest., vol. 74, 843-848, Sep. 1984.

Terranova et al., "Regulation of Cell Attachment and Cell Number" by Fibroectin and Laminin, J. Cell. Physiology 127:473-479, 1986.

Kleinman et al., "Indentification of a Second Active Site in Laminia for Migration and Inhibition of in vivo Melanoma Lung Colonization", Archives of Biochem & Biophys, 272, No. 1:39–45(1989).

Graf et al., "A Pertapeptide from the Laminum Bi Chem. Mediates Cell Adhesion & Birds 67,000 Laminin Receptor", Bio–Chem 26:6896–6900(1987).

*Primary Examiner*—David J. Isabella
*Assistant Examiner*—Debra S. Brittingham
*Attorney, Agent, or Firm*—Birch, Stewart, Kolasch & Birch

[57] ABSTRACT

Peptides with laminin activity are provided as follows:
tyrosine-isoleucine-glycine-serine-arginine;
proline-aspartine-serine-glycine-arginine; and
cysteine -aspartate-proline-glycine-tyrosine-isoleucine-glycine-serine-arginine.

These peptides block angiogenesis, alter the formation of capillary structures by endothelial cells, prevent the formation of excess blood vessels in tissues, and inhibit in vivo tumor cell colonization of tissues.

60 Claims, 5 Drawing Sheets

FIG.1

PEPTIDES WITH LAMININ ACTIVITY

FIELD OF THE INVENTION

This application is a continuation-in-part of application Ser. No. 102,991, filed Oct. 1, 1987, now abandoned which is a continuation-in-part of application Ser. No. 013,919, filed Feb. 12, 1987, now abandoned.

BACKGROUND OF THE INVENTION

Laminin (Mr=900,000) is a large glycoprotein specific to basement membranes. Laminin has been shown to promote cell adhesion, cell growth, cell migration, neurite outgrowth, cell differentiation, and to influence the metastatic behavior of tumor cells. Laminin binds to type IV collagen, heparin, gangliosides, and cell surface receptors and promotes the adhesion and growth of various epithelial and tumor cells as well as neurite outgrowth. Laminin is thought to mediate cell-matrix interactions and to be a structural component of all basement membranes binding to collagen IV, heparan sulfate proteoglycan, and nidogen-entactin.

The laminin molecule itself has a cross-like shape when examined by microscopy, with three short arms and one long arm. Two small globules can be observed at the end of each short arm, and a larger globule can be observed at the end of the long arm. Current models suggest that laminin contains one A chain (Mr=440,000), one B1 chain (Mr=225,000), and one B2 chain (Mr=205,000), with part of each chain forming a short arm and the rest of the chain projecting down the long arm.

Laminin exhibits a number of biological activities, including promoting the attachment, migration, and differentiation of certain cells. Some progress has been made in assigning domains in laminin to its activities. Collagen IV binding is attributed to the globules at the end of the short arm. Cell binding is attributed to the portion of laminin minus the long arm and globules. A site in the long arm of laminin is thought to promote axonal outgrowth. Most of the alpha-helical elements in the laminin molecule have been localized to the portion of the long arm adjacent to the terminal globule. The size of the molecule plus difficulty in separating its chains have impeded further characterization of laminin's structure by conventional chemical approaches.

Active domains have been localized in laminin, based on recent progress in cloning the laminin chains. The B1 chain comprises some 1786 amino acids which appear to form at least six contiguous structural domains. Domains I and II are predominantly alpha-helical and probably extend down the long arm. Domains III and V contain homologous repeats rich in cysteine, and could form rather rigid structures adjacent to the globules formed by domains IV and VI. Studies by the present inventors indicate that a sequence of some five to nine amino acids in domain III is at least partly responsible for the cell attachment, chemotactic, and receptor binding activities of laminin. This sequence also has antimetastatic activity with tumor cells.

SUMMARY OF THE INVENTION

It is an object of the present invention to provide peptides which have useful biological activity.

It is a further object of the present invention to provide peptides which have the biological activity of laminin.

It is yet a further object of the present invention to provide peptides which have biological activity in the field of cell adhesion and migration and blocking of tumor metastases.

It is yet another object of the present invention to provide peptides which block angiogenesis.

It is yet another object of the present invention to provide peptides which alter the formation of capillary structures by endothelial cells.

It is a further object of the present invention to provide peptides which prevent an excess of blood vessels in tissues due to inflammation or other pathological conditions due to Kaposi sarcoma.

It is still a further object of the present invention to provide peptides which inhibit in vivo tumor cell colonization of tissues.

Three peptides have been found to have particularly useful properties: two pentapeptides and a nonapeptide, although several other related peptides were nearly as active as the pentapeptide and the nonapeptide.

The pentapeptides of the present invention have the following amino acid sequences:

tyrosine-isoleucine-glycine-serine-arginine (YIGSR)
proline-aspartine-serine-glycine-arginine (PDSGR-$NH_2$).

In addition, cyclization of YIGSR increases its activity up to two-fold in vitro and in vivo in blocking melanoma cell colonization of the lungs.

PDSGR-$NH_2$ is active in promoting cell adhesion and migration and in reducing the number of melanoma lung colonies in vivo, and also blocks laminin-mediated cell adhesion and migration without affecting fibronectin-mediated activities. Thus, PDSGR-$NH_2$ is specific for laminin activity.

The nonapeptide of the present invention has the following amino acid sequence:

cysteine-aspartate-proline-glycine-tyrosineisoleucine-glycine-serine-arginine (CDPGYIGSR)

The entire primary peptide sequence of one of the chains of laminin was determined from cDNA cloning. Using synthetic peptides prepared on a peptide synthesizer, the active domain on the B1 chain responsible for cell attachment and cell migration was identified. Peptides of 20 amino acids and their corresponding antibodies were prepared to each of the seven structural domains. None of these peptides was active, although one of the antibodies blocked cell attachment. Smaller synthetic peptides were prepared to the region around the amino acid sequence specific to this active antibody. A nine amino acid peptide was found to be directly active in cell attachment and cell migration. Various combinations of smaller peptides which authentically matched the protein sequence and/or contained substitutions were tested until the peptides of the present invention were found.

BRIEF DESCRIPTION OF THE DRAWINGS

FIG. 1 shows the sequence of domain III from the B1 chain of laminin showing the synthetic peptide prepared and studied. Peptides shown above the sequence were inactive, whereas those below it are active.

DETAILED DESCRIPTION OF THE INVENTION

Figure 2:
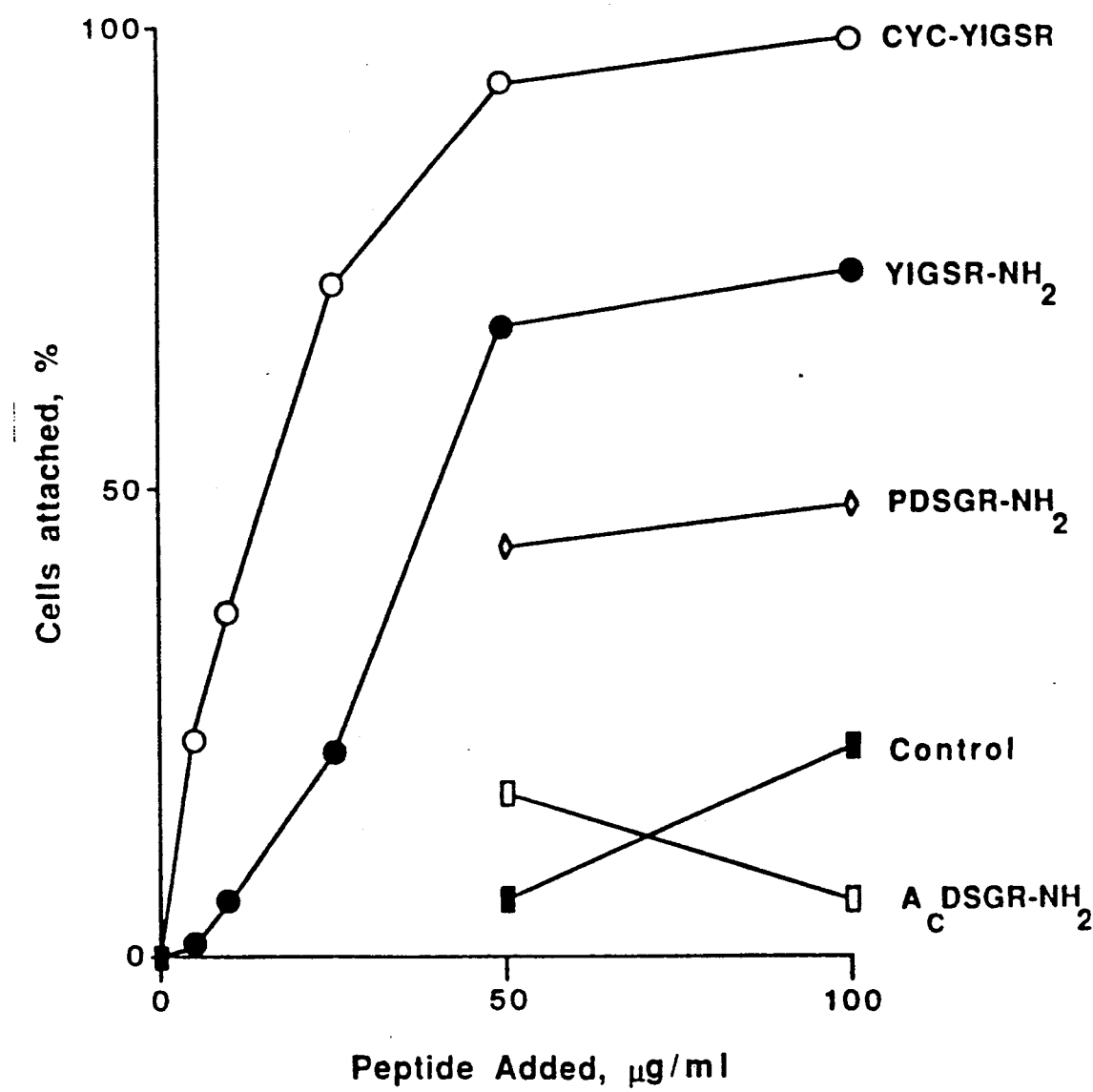
FIG. 2 shows the effect of synthetic peptides on HT-1080 cell adhesion.

Laminin was prepared from the EHS tumor according to established procedures, cf. Timpl et al, *J. Biol. Chem.* 254: 9933-9937 (1979). Fibronectin was prepared by gelatin affinity chromatography of human serum as described by Hopper et al, *Immunology* 30:2490259 (1976) and Engvall et al., *Int. J. Cancer* 1-17 (1977). The peptides were synthesized using an automated Model 430A Applied Biosystems Synthesizer. Deprotection and release of the peptides form the solid phase support matrix were accomplished by treating the protected peptide on the resin with anhydrous HF containing 10% thioanisole or 10% ethyl acetate of diethyl ether at 0° C. to remove the deprotected reagents. The composition and the purity of all peptides were determined by amino acid and HPLC analyses.

The peptide YIGSR, prepared as disclosed in Ser. No. 102,991 and Ser. No. 013,919, which applications are herein incorporated by reference, was cyclized using two methods. Both of these methods involve the incorporation of either chloroacetyl or bromoacetyl moieties at the amino termini of the YIGSR peptide.

METHOD 1

Synthesis of Chloroacetylglycylglycine-Tyr-Ile-Gly-Ser-Arg-Cys-NH$_2$ (ClAcG—G—Y—I—G—S—R—C—NH$_2$)

The N-chloroacetyl-derivatized YIGSRC-NH$_2$ was synthesized according to the method of Lindner and Robey, *Int. J. Peptide Protein Res.* 30: 794-800, 1987. Briefly, in addition to the predetermined amino acid sequence of the desired peptide, N-chloroacetylglycylglycine was incorporated at the amino terminus using the following conditions for automation on the Applied Biosystems, Inc. Model 430A Peptide Synthesizer:

2.0 mmoles of N-chloroacetylglycylglycine per 0.5 mmole of YIGSRC was added to each of two blank amino acid cartridges, and the instrument was programmed to perform the same double coupling procedure as that which is used to couple arginine to a peptide. Because N-chloroacetylglycylglycine is soluble in DMF, the coupling to the amino terminus was performed via the active ester formation using DCC with HOBT in DMF.

Synthesis of Cyclic Gly—Gly—Tyr—Ile—Gly—Ser—Arg—Cys—NH$_2$

Cyclization of ClAcG—G—Y—I—G—S—R—C—NH$_2$ was accomplished by placing 1.0 mg ClAcG—G—Y—I—G—S—R—C—NH$_2$ in 1 ml 0.1M sodium bicarbonate and allowing this solution to sit overnight at room temperature. After this time, the, reaction was complete, as shown by the absence of sulfhydryl groups. The entire solution was clarified by filtration and loaded onto a C$_8$ column equilibrated in 0.1% TFA for preparative reverse phase high performance liquid chromatography (HPLC).

Reverse phase preparative HPLC for purification of cyclic G—G—Y—I—G—S—R—C—NH$_2$ are the following:

Solvent A, 0.1% TFA
Solvent B, 70% acetonitrile in 0.1% TFA.

A linear gradient is run over thirty minutes of 0-100% B. The flow rate is 20 mL/minute. The eluant is monitored at 210 nm. The composition of the cyclic material is confirmed by analytical reverse phase HPLC and by amino acid analysis using the Picotag method of analysis where, after hydrolysis of the cyclized material, S-carboxymethylcysteine is quantitatively determined and is equal to the predicted value of 1 mole per mole of cyclic peptide.

METHOD 2:

Synthesis of N-bromoacetyl—Y—I—G—S—R—C—NH$_2$

Bromoacetic acid was reacted with the N-terminal amine to from the N-bromoacetyl-derivatized Y—I—G—S—R—C—NH$_2$ using the following conditions for automation: 2.0 moles of bromoacetic acid were added to an empty glycine cartridge and the instrument was allowed to follow the program for synthesis as though it were adding a glycine amino acid to the peptide. Deprotection and release of the peptides from the PAM resins was accomplished using anhydrous hydrogen fluoride with 10% anisole at 0° for one to two hours. Following ethyl acetate extraction of the residual peptide-resin mixture, the peptides were extracted with 0.1M aqueous acetic acid and separated form the resin on a sintered glass filter. After lyophilization of the filtrate, the crude peptides were generally obtained in yields of between 85 and 95%.

Synthesis of Cyclic Y—I—G—S—R—C—NH$_2$

Cyclization of the Y—I—G—S—R—C—NH$_2$ peptide occurs by placing 1.0 mg of the bromoacetylated peptide into 1.0 mL of 0.1M NaHCO$_3$ buffer. The reaction was allowed to proceed for one hour at room temperature, after which time all of the sulfhydryl groups disappeared. The cyclic Y—I—G—S—R—C—NH$_2$ was purified as given in method 1 for cyclization.

Cells and Cell Adhesion

HT-1080 cells from a human fibrosarcoma were maintained in Dulbecco's Modified Eagle's Medium supplemented with 10% fetal calf serum. Cells at approximately 80% confluency were released with trypsin, collected by low speed centrifugation, and resuspended in Eagle's Minimal Essential Medium (EMEM) containing 0.02% bovine serum albumin (BSA). Cell attachment assays were performed as previously described using 16 mm Falcon tissue culture wells precoated with the peptides in EMEM containing 0.02% BSA. Cells (10$^5$ in 0.1 ml) were added to the wells and incubated for 90 minutes at 37° C. Subsequently, the wells were washed three times to remove unattached cells, and the attached cells were trypsinized and counted electronically. These peptides were tested at various concentrations in duplicate and each assay was repeated twice, in which the variation between duplicates was less than 15 percent. In the competition assays, peptides were premixed with aliquots of the cells prior to adding cells plus peptide to a laminin (1 microgram/dish)coated dish.

Cells and Cell Migration

B16F10 melanoma cells were used for these cell migration assays. The cell migration assays were carried out using Boyden chambers. To assess the chemotactic activity of the peptides, the peptides were dissolved in serum-free DMEM with 0.1% BSA and added to the lower well. Cells in an amount of 3×10/0.8 ml were placed in the upper compartment and incubated for five hours at 37° C. The cells on the upper side of the filter were mechanically removed, the filter was fixed, stained, and the cells on the lower surface of the filter were counted. Each sample was assayed in quadruplicate, and the cells in at least five microscopic fields per filter were counted. Each assay was repeated two times. To test peptides for their ability to compete with either fibronectin (20 micrograms/ml) or laminin (20 micrograms/ml) as chemoattractants, either protein was placed in the lower compartment and cells plus various peptides were placed in the upper compartment.

In Vivo Pulmonary Tumor Assay

Peptides were solubilized at 2 mg/ml in 0.02M sodium phosphate, pH 7.4, containing 0.15M NaCl (PBS) and mixed with B16F10 cells (5×10) in a final volume of 0.2 ml and injected into the tail vein of C57BL/6 female mice six weeks of age. Three weeks after the injection, the mice were sacrificed and the number of tumors on the surface of the lungs was counted. Eight mice were used for each concentration of peptide tested.

Figure 1:
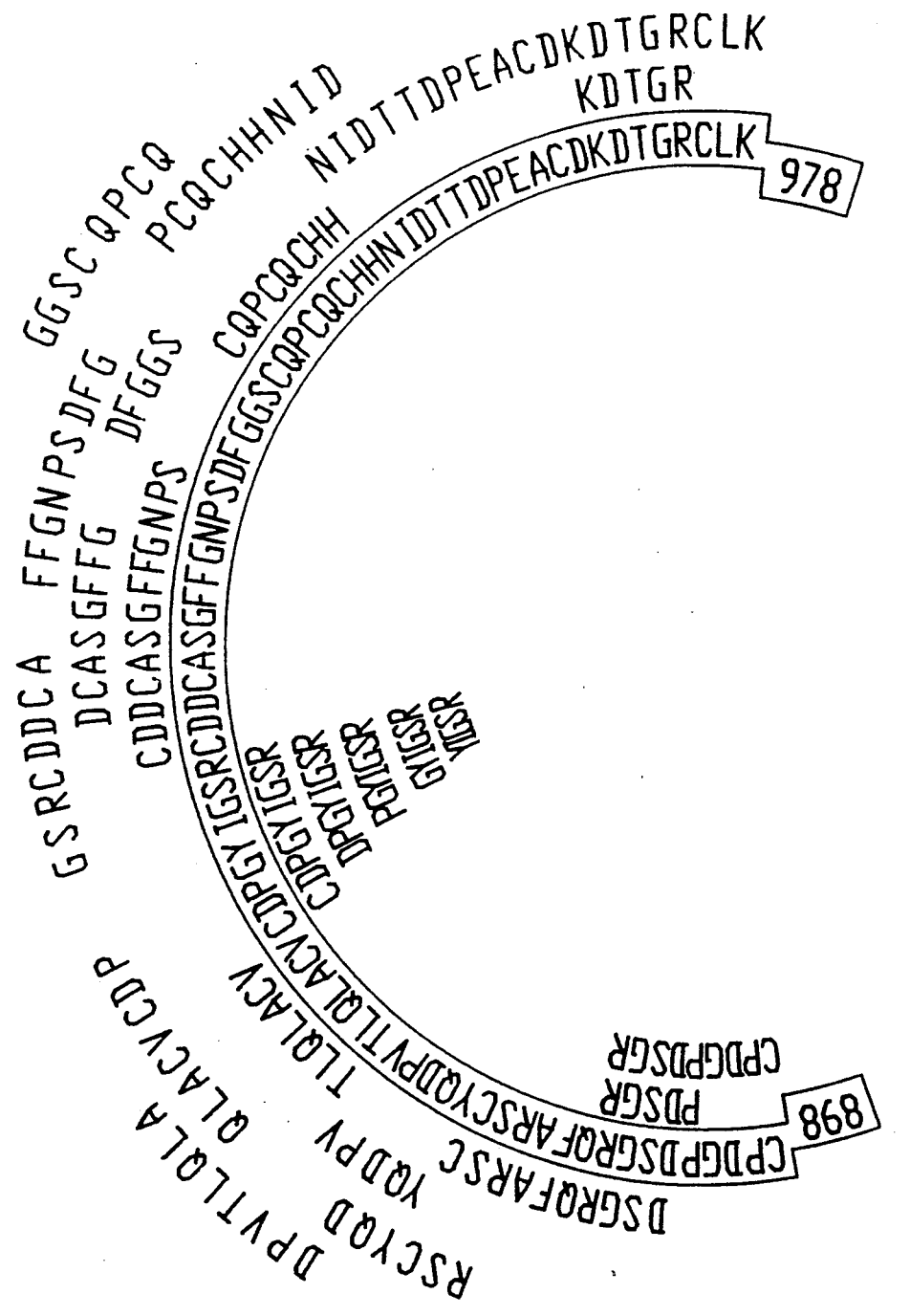

As seen in FIG. 1, various peptides along the sequence in domain III of the B1 chain of laminin were prepared and tested for promotion of cell adhesion using HT-1080 cells. An attempt was made to bracket adjoining peptides by assaying peptides that overlapped each other. Two regions of the sequence in domain III were found to serve for cell attachment: YIGSR and PDSGR, some 20 amino acids toward the N terminus of the chain.

FIG. 2 shows the effect of synthetic peptides on HT-1080 cell adhesion. Various amounts of peptides were dried onto the petri dish and the adhesion of HT-1080 cells after 1.5 hours was determined. Attachment was determined relative to a laminin (5 micrograms.dish) control which was considered to be 100%. Cyclized YIGSR remained the most active form even when cyclized by different techniques. Each peptide concentration was assayed in duplicate, and the results did not differ by more than 15%. The control peptide used was KQADEDIQGTQNLLTSIES.

In this test, PDSGR-$NH_2$ was found to have considerable cell adhesion activity when coated directly onto the petri dish. The PDSGR-$NH_2$ was active in a dose-dependent manner, but clearly had only 50% of the activity of YIGSR-$NH_2$ and was considerably less active than the cyclized YIGSR.

Figure 3:
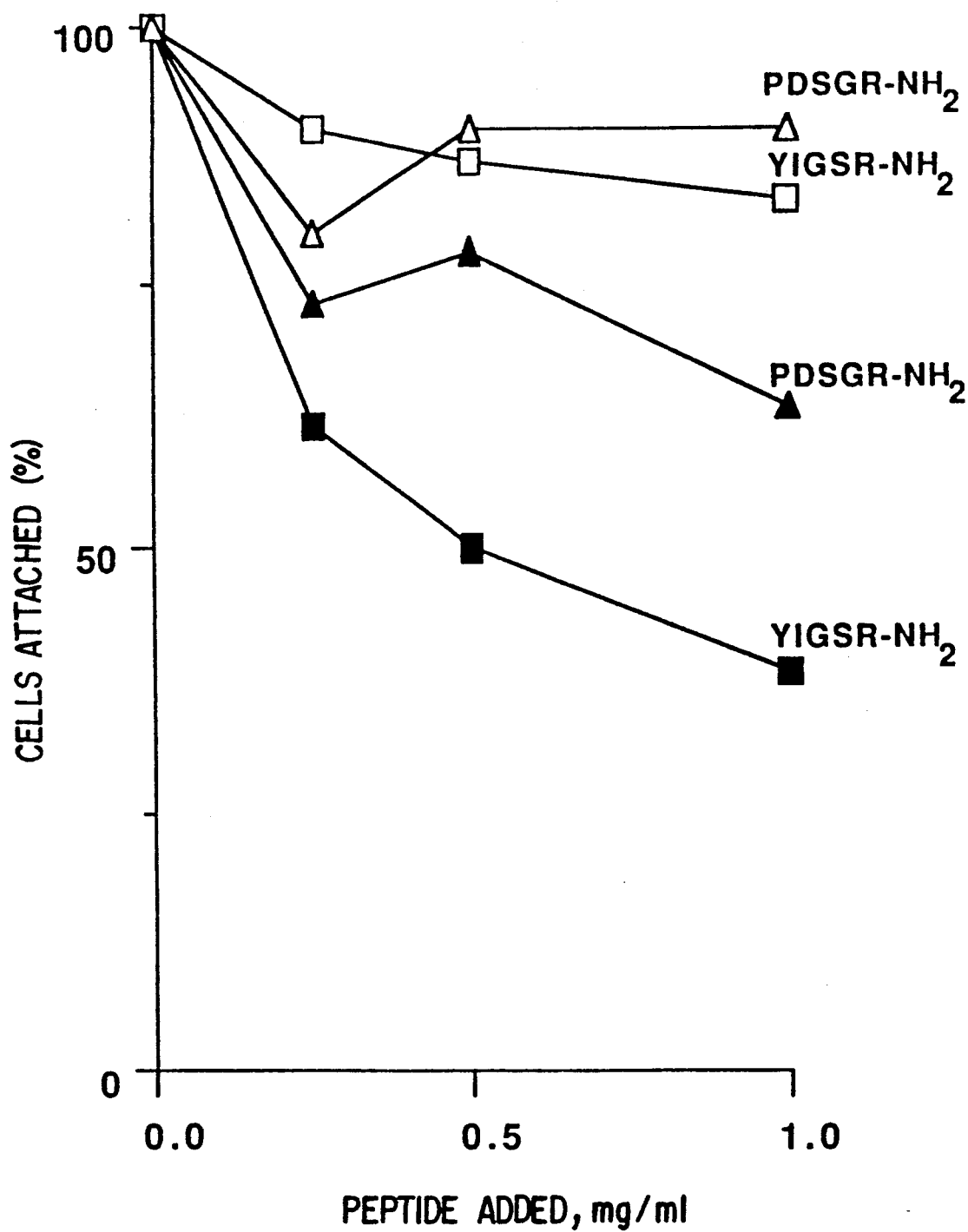
FIG. 3 shows the effect of synthetic peptides on inhibiting HT-1080 cell adhesion to laminin and to fibronectin.

Competition studies were carried out to determine how effectively PDSGR-$NH_2$ could block laminin-mediated cell adhesion and whether it also blocked fibronectin-mediated cell adhesion. Here, increasing amounts of peptide were added in media to dishes already coated with laminin or fibronectin. As shown in FIG. 3, more than twice as much PDSGR-$NH_2$ as YIGSR-$NH_2$ was required to block the adhesion of HT-1080 cells to laminin by 50%. Neither peptide at any dose tested had any effect on cell adhesion to fibronectin substrates. These observations suggest that both peptides are specific for laminin-mediated adhesion.

FIG. 3 shows the effect of synthetic peptides on inhibiting HT-1080 cell adhesion to laminin and to fibronectin. The dishes were first coated with either fibronectin (open symbols) or laminin (closed symbols) for one hour. Then, various amount of each peptide were added. The cells were incubated for 1.5 hour in the dishes and cell adhesion was determined. Each peptide was assayed in duplicate, and the results did not differ by more than 15%.

Figure 4:
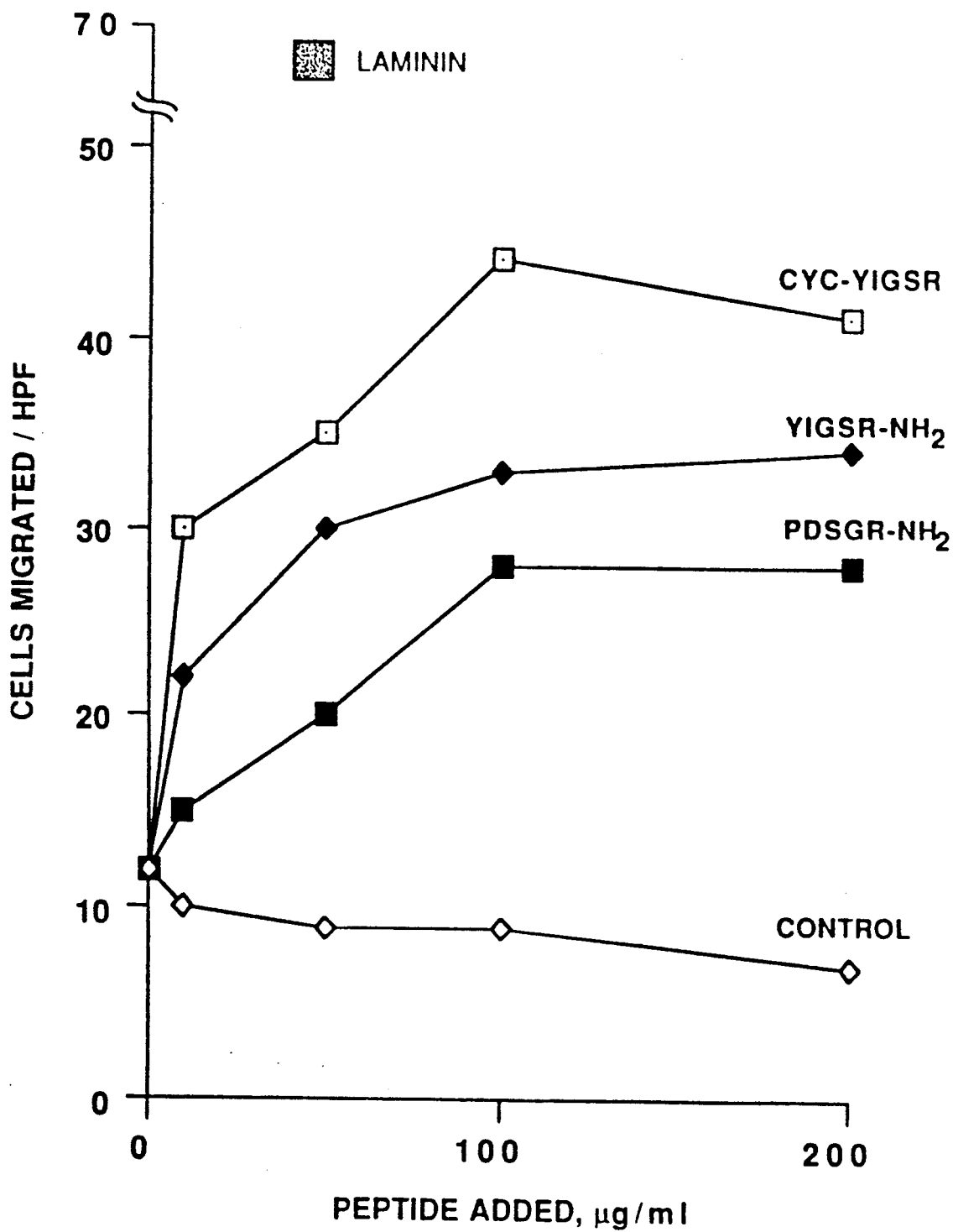
FIG. 4 shows the effect of synthetic peptides on B16F10 melanoma cell migration.
Figure 5:
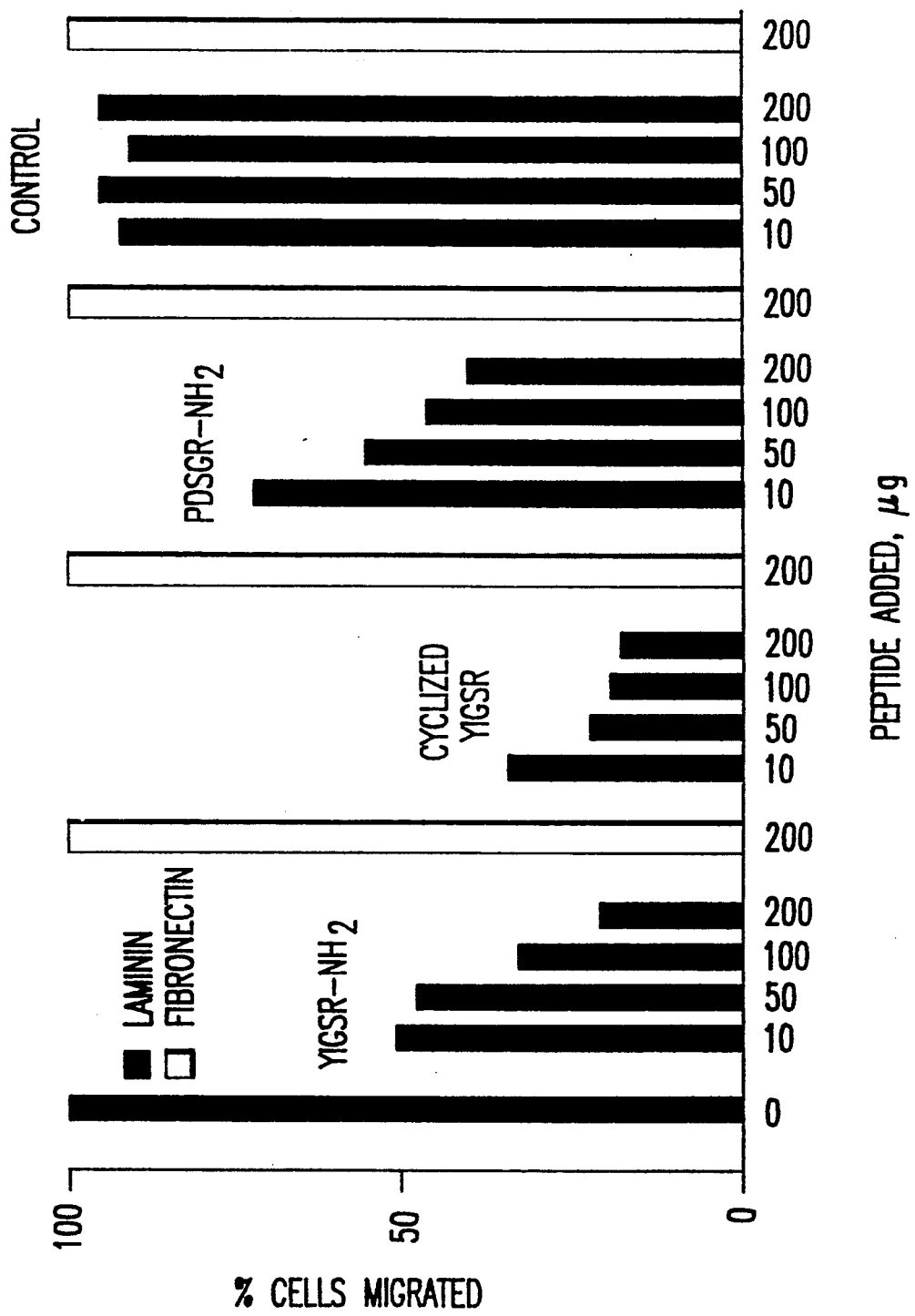
FIG. 5 shows inhibition of cell migration by synthetic peptides.

The various peptides shown in FIG. 1 were also tested for chemotactic activity. These studies showed that the peptides active in cell attachment were also active in chemotaxis as shown in FIG. 4. PDSGR-$NH_2$ showed a dose-dependent stimulation of cell movement, although it was less active than YIGSR-$NH_2$. As expected, both YIGSR-$NH_2$ and PDSGR-$NH_2$ blocked laminin-mediated cell migration in a dose-dependent manner, as shown in FIG. 5. Of the various peptides tested, cyclized YIGSR was the most active. None of the peptides at any concentration inhibited fibronectin-mediated cell migration, indicating further the specificity of these peptides.

To compare the ability of YIGSR-$NH_2$, cyclic YIGSR, and PDSGR-$NH_2$ to block melanoma cell colonization of mouse lungs in vitro, various amounts of the test peptides along with melanoma cells were injected into the tail veins of mice as described above. After three weeks, the mice were sacrificed, and the number of colonies on the surface of the lung was determined by direct counting, as shown in Table 1. The cyclized peptide was the most active, with 76% and 90% inhibition of lung colony formation at 50 micrograms and 100 micrograms per mouse, respectively. PDSGR-$NH_2$ had less activity in inhibiting melanoma lung colonization with 68% and 70% inhibition at 50 and 100 micrograms per mouse, respectively.

TABLE I

Effect of Synthetic Peptides on in vivo Lung Tumor Formation

| Peptide | Amount (μg/mouse) Added | | | |
| --- | --- | --- | --- | --- |
|  | 0 | 50 | 100 | 500 |
| YIGSR-$NH_2$ | >200 | 70 | 45 | 5 |
| cyclic YIGSR | >200 | 32 | 20 | 1 |
| PDSGR-$NH_2$ | >200 | 65 | 60 | 24 |

Data are expressed as number of colonies/lung. Eight mice were for each group. Control peptides were found not to have any effect on reducing the number of lung colonies at all concentrations tested.

FIG. 4 shows the effect of synthetic peptides on B16F10 melanoma cell migration. Various amounts of peptides were added to the lower well of a Boyden chamber and assayed after five hours. Laminin at 20 micrograms/ml served as a positive control. Each peptide concentration was assayed in quadruplicate, and five fields per data point were determined. The control peptide was the same as that used in FIG. 2.

As shown in FIG. 5, various concentrations of each peptide were mixed with the cells in the upper chamber. Inhibition of cell migration to either laminin (closed bars) or fibronectin (20 micrograms each, open bars) was assessed after five hours.

Cyclization of YIGSR greatly increased its activity in all of the assays. It is likely that in this form the peptide had a more stable structure, and that the conformation was favorable for maximal activity. The cyclized YIGSR peptide was considerably more active in the in vivo assay, possibly due to delayed clearance from the circulation as well as a higher affinity for the receptors, which would allow for the peptide to have a greater chance to compete for binding to the cell surface.

The peptides of the present invention can be used as a carrier to target drugs to metastatic tumor cells. Because of this ability to target tumor cells, the peptide can also be conjugated to an anti-cancer agent for therapy.

The peptides of the present invention can be used as a cell-attachment protein to provide substrata to which cells will attach by treating a hydrophobic surface, such as untreated synthetic plastic resin material such as nitrocellulose, or comparable material, with the polypeptide. A similar substratum for cell attachment can be generated by coupling the polypeptide covalently to a solid support, such as glass or a synthetic plastic resin or a long chain polysaccharide, such as agarose, containing a reactive group that can bind the polypeptide. This latter approach can be effected by coupling the peptide to cyanogen bromide-activated agarose beads (sold under the trademark Sepharose by Pharmacia Fine Chemical, Uppsala, Sweden), sterilizing the beads by autoclaving, and thereafter showing that the peptide coating induces attachment of cells to the beads in a concentration greater than can be obtained by passive absorption.

It has also been found that the peptides of the present invention, i.e., those peptides containing the YIGSR (tyrosine-isoleucine-glycine-serine-arginine) sequence, can alter the formation of capillary structures by endothelial cells, and to inhibit angiogenesis (Vascularization). The angiogenesis inhibition was demonstrated in a commonly used assay using chick chorioallantoic membrane.

Human skin endothelial cells plated onto matrigel, a reconstituted basement membrane, which is the subject of patent application Ser. No. 161,867, which is incorporated herein by reference, rapidly aligned and formed capillary-like structures. The cells showed a very different behavior on plastic- or collagen-coated surfaces, forming a monolayer of single cells. More importantly, the addition of YIGSR amide to the media of cells plated on matrigel, or the inclusion of this peptide (YIGSR amide) within the gel, inhibited the endothelial cells from forming capillary-like structures. The peptides of the present invention can be used for preparing surfaces for optimal cell culture, derivatization of various prosthetic materials to promote bonding with surrounding tissues, providing for the increased internalization of molecules such as toxins, drugs, hormones, or the like by the enhancement of phagocytosis, and the development of ways of manipulating cellular adhesion mechanisms in diseases such as cancer metastasis and platelet aggregation.

Such substrata are useful in cell cultures where it is desirable to ensure proper attachment of the cells. Attachment proteins such as laminin have been shown to be important for the growth of many types of cells in vitro. Chemically defined media are often supplemented by attachment proteins (cf. Barnes et al., Cell 22: 649–655, 1980). Coating of the culture substratum with the cell-attachment peptide would obviate the use of laminin in the medium, thus providing better defined conditions for the culture, as well as better reproducibility. An example of the commercial use of cell attachment surfaces is the Cytodex particles manufactured by Pharmacia, wherein the particles are coated with gelatin, making it possible to grow the same number of adherent cells in a much smaller volume of media than would be possible in dishes. The activity of these beads is, however, dependent upon the use of laminin in the growth medium in most cases. The cell-attachment peptide of the present invention should provide a chemically defined coating for such purposes.

Medical devices can be designed which make use of such substrata to attract cells to the surface in vivo or even to promote the growing of a desired cell type on a particular surface prior to grafting. An example of this is endothelial cell growth on a prosthetic blood vessel or vascular graft, which is generally woven or knitted from polyester fiber, particularly Dacron fiber (a polyethylene terephthalate). Because most types of cells are attracted to laminin and to the peptides of the present invention, the peptides of the present invention are useful in coating a patch graft or the like for aiding wound closure and healing following an accident or surgery. The peptides of the present invention can also be used in coating surfaces of a prosthetic device which is intended to serve as a temporary or semipermanent entry into the body., e.g., into a blood vessel or into the peritoneal cavity, sometimes referred to as a percutaneous device. In such cases, it may be advantageous to couple the peptide to a biological molecule, such as collagen, a glycosaminoglycan, or a proteoglycan.

The peptides of the present invention can be administered in amounts ranging from about 10 micrograms to about 20 milligrams per kilogram of body weight.

The peptides of the present invention may be used in the form of a liquid, such as eye drops or lotions, or a salve or gel which may be applied to promote cell attachment, or in any any other convenient form. Accordingly, the peptides may be contained in any pharmaceutically acceptable carrier which is appropriate for the delivery means intended. One manifestation of the cell attachment activity of the peptides of the present invention is their chemotactic activity.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. Peptides having laminin-like activity selected from the group consisting of:
    (1) tyrosine-isoleucine-glycine-serine-arginine;
    (2) cysteine-aspartate-proline-glycine-tyrosine-isoleucine-glycine-serine-arginine;
    (3) aspartate-proline-glycine-tyrosine-isoleucine-glycine-serine-arginine;
    (4) glycine-tyrosine-isoleucine-glycine-serine-arginie;
    and derivatives thereof, said derivatives selected from the group consisting of amides, conjugates with proteins, cyclized peptides, and, polymerized peptides.

2. An anti-metastatic agent for metastatic tumor cells comprising a peptide of claim 1 in a pharmaceutically carrier.

3. The agent of claim 2 wherein the tumor cells are lung carcinoma cells.

4. The agent of claim 2 comprising cyclized tyrosine-isoleucine-glycine-serine-arginine.

5. A carrier to target drugs to metastatic tumor cells comprising a peptide of claim 1 conjugated to an anti-cancer agent.

6. A method for inhibiting the formation of lung metastases comprising administering to an individual having lung cancer an effective amount of a peptide of claim 1.

7. A substrate active in promoting epithelial, endothelial, or neural cell attachment comprising a compound selected from the group consisting of a peptide of claim 1, its amide form, and its bovine serum albumin (BSA) conjugates.

8. A method for promoting increased adhesion of epithelial or endothelial cells to vascular prostheses and other artificial organs comprising coating the prostheses or organs with a composition comprising a peptide of claim 1.

9. The method of claim 8 wherein the peptide is cyclized tyrosine-isoleucine-glycine-serine-arginine.

10. An anti-adhesion factor for laminin-responsive epithelial cells comprising an antibody against a BSA conjugate of a peptide of claim 1.

11. A migration promoting factor for epithelial cells comprising a compound selected from the group consisting of a peptide of claim 1, amides of said peptides, and their BSA conjugates.

12. A method for promoting the migration of epithelial cells in a wound comprising administering to the wound a compound selected from the group consisting of a peptide of claim 1 and the amide forms of said peptides.

13. A migration inhibition factor for laminin responsive epithelial cells comprising a compound selected from the group consisting of a peptide of claim 1, the amide forms of said peptides, and BSA conjugates of said peptides.

14. A method for isolating the laminin cell surface receptor from detergent extracts of cells or of cell membranes bound to a laminin affinity column comprising adding to said cells or cell membranes a compound selected from the group consisting of a peptide of claim 1 and amide forms of said peptides.

15. A prosthetic device having a biolgically active surface which exhibits cell attachment activity, said surface having linked thereto a peptide of claim 1.

16. The prosthetic device of claim 15 wherein said biologically active surface constitutes a portion of a vascular graft.

17. The prosthetic device of claim 15 wherein said biologically active surface contains a synthetic resin fiber.

18. The prosthetic device of claim 15 wherein said biologically active surface comprises a portion of a percutaneous device.

19. A method for inhibiting the formation of blood vessel structures by endothelial cells comprising administering to a patient an effective amount of a peptide of claim 1 or its amide form.

20. A method for treating Kaposi's sarcoma comprising administering to a patient an effective amount of the peptide of claim 1.

21. The peptide of claim 1 which is tyrosine-isoleucine-glycine-serine-arginine.

22. The peptide of claim 21 wherein said derivative is an amide derivative.

23. The peptide of claim 1 with is cysteine-aspartate-proline-glycine-tyrosine-isoleucine-glycine-serine-arginine.

24. The peptide of claim 1 which is aspartate-proline-glycine-tyrosine-isoleucine-glycine-serine-arginine.

25. The peptide of claim 1 which is glycine-tyrosine-isoleucine-glycine-serine-arginine.

26. A peptide having laminin-like activity consisting of the sequence proline-aspartic acid-serine-glycine-arginine and derivatives thereof, said derivatives selected from the group consisting of amides, conjugates with proteins, cyclized peptides, and polymerized peptides.

27. The peptide of claim 26 wherein said derivative is an amide derivative.

28. An anti-metastatic agent for metastatic tumor cells comprising a peptide according to claim 26 in a pharmaceutically acceptable carrier.

29. The agent of claim 28 wherein the tuor cells are lung carcinoma cells.

30. A carrier to target drugs to metastatic tumor cells comprising a peptide according to claim 26 conjugated to an anti-cancer agent.

31. The method of claim 6 wherein the derivative of said peptide is an amide derivative.

32. A method for inhibiting the formation of lung metastases comprising administering to an individual having lung cancer an effective amount of a peptide according to claim 26.

33. The method of claim 49 wherein the derivative of said peptide is an amide derivative.

34. A substrate active in promoting epithellial, endothelial, or neural cell attachment comprising a compound selected from the group consisting of a peptide of claim 26, its amide form, and its BSA conjugates.

35. The method of claim 8 wherein the derivative of said peptide is an amide derivative.

36. A method of promoting increased adhesion of epithelial or endothelial cells to vascular prostheses and other artificial organs comprising coating the prostheses or organs with a composition comprising a peptide according to claim 26.

37. The anti-adhesion factor of claim 10 wherin the antibody is specific to the B-chain of laminin.

38. A migration promoting factor for epithelial cells comprising a compound selected from the group consisting of a peptide according to claim 26, amides of said peptides, and their BSA conjugates.

39. A method for promoting the migration of eqithelial cells in a wound comprising administering to the wound a compound selected from the group consisting of a peptide according to claim 26 and amide forms of said peptides.

40. A migration inhibition factor for laminin responsive epithelial cells comprising a compound selected from the group consisting of a peptide according to claim 26, amide forms of said peptide, and BSA conjugates of said piptide.

41. A method for isolating the laminin cell surface receptor from detergent extracts of cells or of cell membranes bound to a laminin affinity column comprising adding to said cells or cell membranes compound selected from the group consiting of a peptide according to claim 26 and amide forms of said peptide.

42. A prosthetic device having a biologically active surface which exhibits cell attachemnt activity, said surface having linked thereto a peptide according to claim 26.

43. The prosthetic device of claim 42 wherein said biologically active surface constitutes a portion of a vascular graft.

44. The prosthetic device of claim 42 wherein said biologically active surface contains a synthetic resin fiber.

45. The prosthetic device of claim 42 wherein said biologically active surface comprises a portion of a percutaneous device.

46. A composition comprising a solid substrate having attached thereto a peptide according to claim 1.

47. The composition of claim 46 wherein the solid substrate is selected from the group consisting of nitrocellulose and polyester.

48. The composition of claim 46 wherein the solid substrate is agarose.

49. A composition comprising a solid substrate having attached thereto a peptide according to claim 26.

50. The composition of claim 49 wherein the solid substrate is selected from the group consisting of nitrocellulose and polyester.

51. The composition of claim 49 wherein the solid substrate is agarose.

52. A composition comprising a peptide according to claim 1 coupled to collagen.

53. The composition of claim 52 further comprising a pharmaceutically acceptable carrier.

54. The composition of claim 53 which is in a form selected from the group consisting of a lotion, salve, gel, colloid, and powder.

55. A composition comprising a peptide according to claim 26 coupled to collagen.

56. The composition of claim 55 further comprising a pharmaceutically acceptable carrier.

57. The composition of claim 56 which is in a form selected from the group consisting of a lotion, salve, gel colloid, and powder.

58. A method for inhibiting the formation of blood vessel structures by endothelial cells comprising administering to a patient an effective amount of a peptide according to claim 26 or its amide form.

59. A method for treating Kaposi's sarcoma comprising administering to a patient an effective amount of a peptide according to claim 26.

60. The peptide of claim 21 which is cyclized tyrosine-isoleucine-glycine-serine-arginine.

* * * * *